(12) United States Patent
Tawil

(10) Patent No.: US 12,396,460 B2
(45) Date of Patent: Aug. 26, 2025

(54) BACTERIAL CONTROL THROUGH DISPERSION OF BACTERIOPHAGE POWDERS

(71) Applicant: PHAGELUX CANADA INC., Montreal (CA)

(72) Inventor: Nancy Tawil, Cantley (CA)

(73) Assignee: PRECISIO BIOTIX THERAPEUTICS, INC., Dover, DE (US)

( * ) Notice: Subject to any disclaimer, the term of this patent is extended or adjusted under 35 U.S.C. 154(b) by 363 days.

(21) Appl. No.: 17/438,742

(22) PCT Filed: Jun. 16, 2020

(86) PCT No.: PCT/IB2020/055625
§ 371 (c)(1),
(2) Date: Sep. 13, 2021

(87) PCT Pub. No.: WO2020/254967
PCT Pub. Date: Dec. 24, 2020

(65) Prior Publication Data
US 2023/0363396 A1 Nov. 16, 2023

Related U.S. Application Data

(60) Provisional application No. 62/862,178, filed on Jun. 17, 2019.

(51) Int. Cl.
*A01N 63/40* (2020.01)
*A01N 25/12* (2006.01)
(Continued)

(52) U.S. Cl.
CPC ............. *A01N 63/40* (2020.01); *A01N 25/12* (2013.01); *A01P 1/00* (2021.08); *A61L 2/23* (2013.01); *A61L 2/26* (2013.01)

(58) Field of Classification Search
CPC .......... A01N 63/40; A01N 25/12; A01P 1/00; A61L 2/23; A61L 2/26; A61L 2202/25; C12N 2795/00011
See application file for complete search history.

(56) References Cited

U.S. PATENT DOCUMENTS 8,501,453 B2    8/2013   Walbeck
8,889,105 B2   11/2014   Finlay et al.
(Continued)

OTHER PUBLICATIONS

Written Opinion of the International Searching Authority issued by the World Intellectual Property Organization on Sep. 20, 2020 for PCT application PCT/IB2017/055625 from which the present application is a national phase.

(Continued)

*Primary Examiner* — Regina M Yoo

(57) ABSTRACT

A method of eliminating, reducing or preventing bacterial contamination of a surface, the method comprising dispersing a bacteriophage containing composition in air in proximity to the surface. In some embodiments, the bacteriophage containing composition is a powder dispersed by pressurizing a load chamber containing the powder so that the powder is expelled through an outlet. Also, devices for performing the method and a powder used in the method.

22 Claims, 9 Drawing Sheets

(51) Int. Cl.
*A01P 1/00* (2006.01)
*A61L 2/23* (2006.01)
*A61L 2/26* (2006.01)

(56) References Cited

U.S. PATENT DOCUMENTS

| | | | |
|---|---|---|---|
| 9,134,312 B2* | 9/2015 | Da Costa Garcia ... | A61K 35/76 |
| 9,682,110 B2* | 6/2017 | Da Costa Garcia ... | A61K 35/76 |
| 10,772,964 B2 | 9/2020 | Katsarava | |
| 10,849,944 B2 | 12/2020 | Tawil et al. | |
| 2009/0130196 A1 | 5/2009 | Murthy et al. | |
| 2012/0052048 A1* | 3/2012 | Da Costa Garcia . | A61K 9/0014 |
| | | | 435/235.1 |
| 2014/0079671 A1* | 3/2014 | Da Costa Garcia .... | A61P 17/00 |
| | | | 435/235.1 |
| 2019/0359947 A1 | 11/2019 | Shaw et al. | |

OTHER PUBLICATIONS

International Search Report issued by the World Intellectual Property Organization on Sep. 20, 2020 for PCT application PCT/IB2017/055625 from which the present application is a national phase.

González-Menéndez E, Fernández L, Gutiérrez D, Rodríguez A, Martínez B, García P, Comparative analysis of different preservation techniques for the storage of *Staphylococcus phages* aimed for the Industrial development of phage-based antimicrobial products. PLoS One Oct. 2018 13(10): e0205728.

Golshahi, L., Lynch, K., Dennis, J. and Finlay, W., In vitro lung delivery of bacteriophages KS4-M and φKZ using dry powder inhalers for treatment of Burkholderia cepacia complex and Pseudomonas aeruginosa infections in cystic fibrosis. Journal of Applied Microbiology, Sep. 2010, 110: 106-117.

Arora, A. Liquid and Powder Jet Injectors in Drug Delivery: Mechanisms, Designs, and Applications, Percutaneous Penetration Enhancers Physical Methods in Penetration Enhancement, Jan. 2017 vol. 14, pp. 221-230.

Newman, SP Principles of metered-dose inhaler design, Respir Care Sep. 2005;50(9):1177-90.

Masuda H., Dry dispersion of fine particles in gaseous phase, Advanced Powder Technology, Mar. 2009, vol. 20, Issue 2, pp. 113-122.

* cited by examiner

BACTERIAL CONTROL THROUGH DISPERSION OF BACTERIOPHAGE POWDERS

FIELD OF THE INVENTION

The present invention relates to the general field of bacteriophages and is more particularly concerned with bacterial control through dispersion of bacteriophage powders.

BACKGROUND

Prevention and elimination of bacterial contamination is important in many contexts, for example in hospital settings. Current methods of reducing or eliminating bacterial content in hospital rooms typically involve spraying surfaces with a bactericide solution and wiping the thus sprayed surface manually. As such, they are time consuming, labour intensive, and costly. It is also difficult to achieve a desired degree of decontamination using such methods. In addition, many bactericides have a relatively small effective duration as they are rapidly degraded and may lead to bacterial resistance, both to the specific bactericide used, and to other useful bactericides, such as antibiotics.

It has been proposed to use fogging, a wet process, to disperse bacteriophages in a room. However, fogging may require multiple hours or days depending on the square footage of the facility. This means that patients would need to be removed from the rooms while fogging takes place during that period. Also, many fogging methods are not compatible with bacteriophage viability. The use of fogging chemicals such as $H_2O_2$ is known to impact bacteriophage activity.

Therefore, there is a need to provide novel and improved methods and devices for reducing or preventing bacterial contamination.

An object of the present invention is to provide such methods and devices.

SUMMARY OF THE INVENTION

In a broad aspect, there is provided a method using bacteriophages for at least partially disinfecting a surface exposed to air, the method comprising: providing a powder, the powder including bacteriophages; and dispersing the powder in the air in proximity of the surface to apply at least part of the powder on the surface, wherein the powder is dispersed nonpyrogenically using a dry dispersion mechanism.

There may also be provided a method wherein providing the powder includes providing the powder in a load chamber; and dispersing the powder includes pressurizing the load chamber to a dispersion pressure larger than atmospheric pressure to expel the powder out of the load chamber.

There may also be provided a method wherein pressurizing the load chamber includes introducing a pressurized gas having a gas pressure larger than atmospheric pressure in the load chamber.

There may also be provided a method wherein the load chamber is at least in part destroyed when the pressurized gas is introduced in the load chamber.

There may also be provided a method wherein the powder is expelled out of the load chamber through at least one nozzle in fluid communication with the load chamber.

There may also be provided a method wherein the powder consists essentially of bacteriophages.

There may also be provided a method wherein the bacteriophages are in the form of lyophilized bacteriophage particles.

There may also be provided a method wherein the powder further includes auxiliary particles.

There may also be provided a method wherein the powder includes lyophilized bacteriophage particles dispersed in the auxiliary particles.

There may also be provided a method wherein the lyophilized bacteriophage particles make up from about 1 percent to about 50 percent in mass of the powder.

There may also be provided a method wherein the auxiliary particles are selected from the group consisting of inorganic salt particles, hydrophobic polymer particles, silica particles, polyvinylpyrrolidone particles, cellulose ethers particles, polyethylene glycol particles, polyvinyl alcohol particles, poloxamers particles $MgSO_4$ particles, $MgCO_3$ particles, $CaCO_3$ particles and talc particles, ionic surfactant particles, non-ionic surfactant particles, magnesium aluminometasilicate particles, cyclodextrins particles, magnesium stearate particles, starch particles, bactericide particles, detergents particles, antibiotics particles, nanoparticles, metallic powders particles, Ag particles, Cu particles, AgCu alloys particles, bimetallic nanoparticles, $FeO_4$ particles, $FeO_3$ particles, FeO particles superparamagnetic particles, and combinations thereof.

There may also be provided a method wherein at least part of the bacteriophages are immobilized on the auxiliary particles.

There may also be provided a method wherein at least 95 percent of the lyophilized bacteriophage particles in particle number has less than about 180 μm in size.

There may also be provided a method wherein at least 95 percent in mass of the lyophilized bacteriophage particles has less than about 180 μm in size.

There may also be provided a method wherein at least 95 percent of the lyophilized bacteriophage particles in particle number has less than about 45 μm in size.

There may also be provided a method wherein at least 95 percent in mass of the lyophilized bacteriophage particles has less than about 45 μm in size.

There may also be provided a method wherein at least 95 percent of the lyophilized bacteriophage particles in number have more than about 10 μm in size.

There may also be provided a method wherein at least 95 percent of the lyophilized bacteriophage particles in mass has more than about 10 μm in size.

There may also be provided a method wherein the load chamber is pressurized to between about 4 MPa and about 7 MPa.

There may also be provided a method wherein dispersing the powder includes aerosolizing the powder.

There may also be provided a method wherein the surface include one of a room surface inside a room, a vehicle surface inside a vehicle, an exposed wound surface, a conduit surface inside a conduit, an outdoors surface in the environment or combinations thereof.

There may also be provided a method further comprising lysing bacteria present on the surface with the bacteriophages.

There may also be provided a method wherein the surface is a surface inside a lung, the method further comprising leading part of the powder inside the lungs through inhalation of the part of the powder after dispersion of the powder.

In another broad aspect, there is provided a device for at least partially disinfecting a surface exposed to air using bacteriophages, the device comprising: a pressurized gas source for providing a pressurized gas at a pressure larger than atmospheric pressure; a load chamber containing a powder, the powder including the bacteriophages; a valve provided between the pressurized gas source and the load chamber, the valve being configurable between a closed configuration in which the pressurized gas is prevented from entering the load chamber and an open configuration in which the pressurized gas is allowed to enter the load chamber to pressurize the latter; and an actuator for selectively moving the valve from the closed to the open configuration; wherein, when the valve is configured from the closed configuration to the open configuration, the pressurized gas enters the chamber and expels the powder therefrom and into the air through an outlet.

There may also be provided a device wherein the outlet is formed by a dispersion head defining at least one nozzle in fluid communication with the chamber.

There may also be provided a device wherein the dispersion head defines a plurality of nozzles configured to cause an omnilateral dispersion of the powder upon pressurization of the load chamber.

There may also be provided a device wherein the dispersion head defines a plurality of nozzles dispersed around a segment of a cylindrical surface covering between about 60 and about 180 degrees.

There may also be provided a device wherein the dispersion head defines a plurality of nozzles dispersed around a segment of a cylindrical surface covering between about 60 and about 120 degrees.

There may also be provided a device further comprising a diaphragm between the load chamber and the dispersion head, the diaphragm being weak enough to burst under pressurization of the load chamber with the pressurized gas when the valve is opened.

There may also be provided a device further comprising a mesh diaphragm between the load chamber and the dispersion head.

There may also be provided a device wherein the load chamber is structurally unable to withstand the pressure of the pressurized gas so that the load chamber is at least partially destroyed when the valve is opened to create the outlet allowing dispersion of the powder in the air.

There may also be provided a device wherein the pressurized gas source includes a compressed gas cartridge.

There may also be provided a device wherein the compressed gas cartridge contains compressed $CO_2$.

There may also be provided a device wherein the actuator is remote controlled.

There may also be provided a device wherein the actuator includes a timer and is operative for moving the valve from the closed configuration to the open configuration after a predetermined delay after activation of the timer.

There may also be provided a device wherein the actuator is operative for repeatedly dispersing a predetermined quantity of the powder at predetermined time intervals by repeatedly opening the valve for a predetermined duration, closing the valve immediately after the predetermined duration and repeating opening and closing of the valve after the predetermined time intervals.

There may also be provided a device wherein the valve is a poppet valve.

There may also be provided a device wherein the powder has one or more characteristics similar to those mentioned with respect to powder of the method described hereinabove.

In yet another broad aspect, there is provided a powder comprising: lyophilized bacteriophage particles; and biologically inactive auxiliary particles; wherein the powder includes between 1% and 50% in mass of the lyophilized bacteriophage particles. The powder may have one or more characteristics similar to those as mentioned with respect to the method described hereinabove.

There may also be provided a powder wherein auxiliary particles are selected from the group consisting of $MgSO_4$ particles, $MgCO_3$ particles, $CaCO_3$ particles and talc particles.

There may also be provided a method There may also be provided a method using bacteriophages for at least partially disinfecting a surface exposed to air, the method comprising: providing a powder, the powder including bacteriophages; and dispersing the powder in the air in proximity of the surface to apply at least part of the powder on the surface, wherein the powder is dispersed nonpyrogenically.

There may also be provided a method of treating a pulmonary bacterial infection in a mammal having lungs, the method comprising: providing a powder, the powder including bacteriophages infectious for bacteria causing the bacterial infection; dispersing the powder in the air, wherein the powder is dispersed nonpyrogenically using a dry dispersion mechanism; and having the mammal inhale the powder to deliver the bacteriophages to the lungs.

The powder and the device described hereinabove may be used to perform this latter method.

Advantageously, the proposed method is rapidly executed and does not depend unduly on the skills of the operator of the proposed device. In opposition to fogging, the proposed method releases the fine particles of the powder almost instantaneously. In some embodiments, it may take as little as a few seconds to disperse the bacteriophages. The proposed method also doesn't require the use of phage-toxic gases.

Furthermore, the use of a solid preparation is advantageous when compared to liquid preparations as liquid bacteriophages or dispersion of liquid particles of phages, are susceptible to quick inactivation at room temperature or at high temperature in developing country settings. Stability of the proposed powdery suspensions including fine particles is typically much greater, in some embodiments over 600 days stability at room temperature. Accordingly, in some embodiments, there is no need for cold-chain and storage at 4° C. Room temperature stability alleviates the need for cold chain packaging, shipping and storage, which significantly decreases price, footprint, and the necessity of having cold rooms, and dependability on electricity in third world settings.

The proposed method differs markedly from, for example, fogging of particles including bacteriophages through faster and more effective deployment. Fogging may require multiple hours or days depending on the square footage of the facility. This means that patients would need to be removed from the rooms while fogging takes place during that period. The proposed method releases the fine particles almost instantaneously. Also, many fogging methods are not compatible with bacteriophage viability. The use of fogging chemicals such as $H_2O_2$ is known to impact bacteriophage activity. The proposed method doesn't require the use of phage-toxic gases.

In addition, fogging requires a control of temperature and humidity to create the aerosol droplets. The proposed method does not require stringent temperature or humidity control and works in a very diverse set of environments. When using fogging, ventilation is required to disperse the droplets in all parts of the room, or a person is required to direct the fog in different spaces and areas. In some embodiments, the proposed method is self-dispersing and doesn't need ventilation. The proposed fine particles can, in some embodiments, be commercialized as disposable units or refill cartridges, which is relatively easy to distribute and use.

Other objects, advantages and features of the present invention will become more apparent upon reading of the following non-restrictive description of preferred embodiments thereof, given by way of example only with reference to the accompanying drawings.

DETAILED DESCRIPTION

Figure 1:
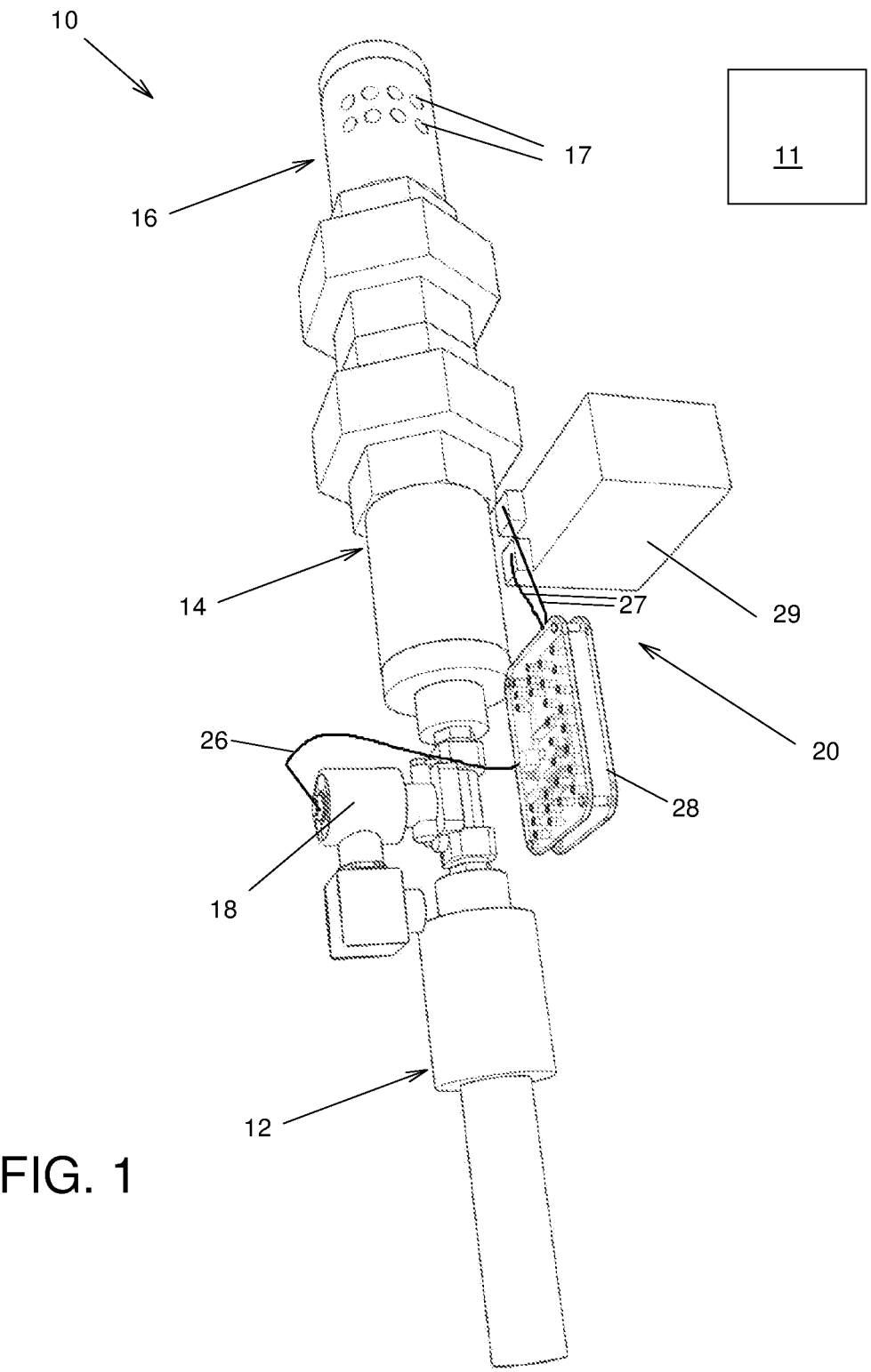
FIG. 1, a perspective view, illustrates a device for dispersing a powder containing bacteriophages in accordance with an embodiment of the present invention.

It is proposed to treat a surface exposed to air to at least partially disinfect the surface, for example by eliminating, reducing or preventing bacterial contamination of the surface using a powder, the powder including bacteriophages. The powder including bacteriophages is referred to herein as "the powder". The bacteriophages may be in the form of lyophilized bacteriophage fine particles, either purely such particles or in the presence of auxiliary particles, or include bacteriophages that are immobilized on fine particles. The fine particles, also referred to simply as "particles" have a dimension small enough to remain suspended in air for a duration long enough that when suspended, the particles can diffuse or move through convection adjacent the surface to treat to eventually contact the surface.

In some embodiments, the powder includes lyophilized bacteriophage particles, or consists essentially of such lyophilized bacteriophage particles, and at least 95 percent in mass or in particle numbers of the lyophilized bacteriophage particles have less than about 180 µm in size or less than about 45 µm in size. In some embodiments, at least 95 percent in mass or in particle numbers of the of the lyophilized bacteriophage particles includes particles having more than about 10 µm in size. If other particles are present in the powder, such as auxiliary particles detailed hereinbelow, the size distribution for the other particles can meet the same limits as the ones mentioned for the lyophilized bacteriophage particles, or the size distribution for the other particles can differ from these limits. For example, having the other particles that are larger than the lyophilized bacteriophage particles may be acceptable or even desirable in some embodiments. For example, larger particles may settle faster and travel less than the bacteriophage particles, but help in the initial dispersion or during manufacturing of the powder.

In some embodiments, the surface to treat is in a room or any other enclosed or mostly enclosed space and most or all of the surfaces present in the room may be treated. Example of such spaces include hospital patient rooms, operating rooms, intensive care units, and other medical treatment facilities. Temporary structures, such as tents, and vehicles, such as ambulances and military vehicles, could also benefit from the proposed treatment method. In other embodiments, the surface to treat is the internal surface of a water or air conduit. In yet other embodiments, the surface to treat is an exposed surface of a wound. In other embodiments, the particles are dispersed outside, in the environment, for example to decontaminate agricultural fields or outdoor surfaces contaminated by biological weapons. The proposed method may also be used to provide respiratory therapy to a patient, a human or a non-human mammal, suffering from a bacterial infection, by dispersing the powder as above and having the patient inhale the powder suspended or aerosolized in the air. In such cases, bacteriophages intended to treat the pulmonary infection are provided.

When auxiliary particles are present, they may include one or more of inorganic salt particles, hydrophobic polymer particles, such as the polymers described in US patent application publication US20160375139A1 published Dec. 29, 2016, the contents of which is hereby incorporated by reference in its entirety, silica, polyvinylpyrrolidone, cellulose ethers, polyethylene glycol, polyvinyl alcohol or poloxamers. Other examples of auxiliary particles include particles of inorganic salts, such as $MgSO_4$, $MgCO_3$, $CaCO_3$ and talc. Yet other example of suitable auxiliary particles include surfactants, ionic or non-ionic. Yet other example of suitable auxiliary particles include magnesium aluminometasilicate, cyclodextrins, talc, magnesium stearate, and starch, and bactericide particles, such as detergents, antibiotics or other bactericides, such as nanoparticles, metallic powders, for example AG, Cu, AGCU alloys, bimetallic nanoparticles, could also be contained in the composition, if compatible with bacteriophage viability. In yet other embodiments, the auxiliary particles include $FeO_4$, $FeO_3$, FeO, superparamagnetic particles, and combinations thereof. In some embodiments, the bacteriophages are adsorbed on the surface of solid particles, lyophilized, spray-dried or dispersed in degradable particles that will experience relatively quick degradation upon contact with the atmosphere or the surface. In some embodiments, the composition replaces the bacteriophages with phage-related products, or includes such phage-related products in addition to the bacteriophages. Examples of such phage-related products include endolysins, phage proteins, phage enzymatic formulations, and combinations thereof.

The particles may be discharged in air in any suitable manner. An advantageous way of performing this discharge is to use a sudden increase in pressure in a container using a compressed gas. In some embodiments, the container is destroyed when the pressure increase is created. In other embodiments, the container includes an exhaust having a shape suitable to allow dispersion of the particles through the exhaust when the pressure is increased in the container. The exhaust may be used to control or influence the direction in which the particles are spread and the speed at which they are ejected.

Referring to FIGS. 1 and 2, there is shown a first embodiment of device 10 for disinfecting a surface 11 (only schematically represented in FIGS. 1 and 2) exposed to air using bacteriophages. The bacteriophages are present in a powder 15 containing the bacteriophages, as detailed hereinabove, and schematically represented in FIG. 2. The device 10 includes a pressurized gas source 12 providing a pressurized gas at a pressure larger than atmospheric pressure a load chamber 14 adjacent the compressed pressurized gas source 12 and a dispersion head 16 in fluid communication with the load chamber 14 and providing an outlet for the powder 15. A valve 18 is provided between the pressurized gas source 12 and the load chamber 14, the valve 18 being configurable between a closed configuration in which the pressurized gas is prevented from entering the load chamber 14 and an open configuration in which the pressurized gas is allowed to enter the load chamber 14 to pressurize the latter. The valve 18 is operated by an actuator 20 that can selectively allow an intended user to move the valve 18 from the closed to the open configuration. When the valve 18 is configured from the closed configuration to the open configuration, the pressurized gas enters the load chamber 14 and expels the powder 15 therefrom and into the air through the dispersion head 16. For example, the load chamber is pressurized at between about 4 MPa to about 7 MPa, for example about 6 MPa, but lower or larger pressures may be used in some embodiments.

The pressurized gas source 12 is of any type that may provide enough gas at enough pressure to cause dispersion of the powder in the air. For example, referring to FIG. 2, the pressurized gas source 12 includes a receptacle 30 defining a gas source chamber 32 thereinto. The gas source chamber 32 is provided with a conventional cartridge opener 34 extending thereacross for opening a conventional compressed gas cartridge 36, such as a CO2 cartridge, contained in the gas source chamber 32. The gas source chamber 32 for example defines an axial aperture 38 allowing insertion of the compressed gas cartridge 36 thereinto and may be closed with a screwable cap 40 inserted in the axial aperture. Screwing the cap 40 pushes the compressed gas cartridge 36 towards the cartridge opener 34, which breaks the conventional seal on the compressed gas cartridge 36 and pressurized the whole gas source chamber 32.

In some embodiments, the compressed gas cartridge 36 is replaced after each use or after a predetermined number of uses of the device 10. The compressed gas cartridge 36 is therefore provided filled with a compressed gas and discarded or sent for refilling when the pressure in the compressed gas cartridge 36 is too low.

In other embodiments (not shown in the drawings), the pressurized gas source 12 includes a chamber that can be pressurized using a compressed gas, for example through a commercial compressed gas cylinder. Other manners of providing the compressed gas are also within the scope of the appended claims.

As seen in FIGS. 1 and 2, in some embodiments, the pressurized gas source 12, load chamber 14 and dispersion head 16 have a generally cylindrical shape and are screwed to each other to allow easy disassembly and assembly of the device 10. In other embodiments, most of the components of the device 10 are permanently attached to each other, and only the end cap 40 and one junction of the load chamber 14, either in the load chamber 14 itself, or at one end thereof, can be unscrewed to respectively allow insertion of the gas cartridge 36 in the gas source chamber 32 and insertion of the powder 15 in the load chamber 14.

Referring to FIG. 1, in some embodiments, the actuator 20 is of the type including a controller 28 operative for allowing a power source 29, such as a battery, to power electro-mechanical valve 18, to open the valve 18 to allow the pressurized gas to reach the powder 15 for dispersion. The controller 28 may be a simple push button connected through wires 27 to the power source 29, that, when activated, transmits an electrical signal, through another wire 26, to an electro-mechanical valve 18 that release the pressure from the compressed gas source 12 into the load chamber 14 when the electrical signal is received. However, the actuator 20 may be also wireless, and responsive to opening the valve 18 when a predetermined wireless signal is received, or mechanical. In some embodiments, the controller 28 includes circuitry providing a timer characteristics allowing to activate the device 10 and then leave so that the user of the device 10 is not exposed to a large concentration of powder 15 and does not affect the dispersion of the powder 15.

In yet other embodiments, the controller 28 is operative for periodically dispersing a predetermined quantity of the powder 15 at predetermined time intervals. For example, the controller 28 includes a microcontroller running software operative for periodically opening the valve 18 for a predetermined duration and immediately after closing the valve 18. These periodic dispersals of the powder 15 may for example be performed many times before there is a need to reload the load chamber 14, or the device 10 may then be provided with a powder dispenser that refills the load chamber 14 after each powder 15 dispersal. For example the powder dispenser includes a container containing the powder 15 and is provided with an access door leading into the load chamber 14, so that the access door may be opened to reload the load chamber 14 each time the device 10 has dispersed the powder 15. Other suitable mechanisms for refilling the load chamber 14 automatically may also be used. Periodic dispersal may be performed in "burst" mode, wherein pressurization of the load chamber 14 is performed at intervals of a few seconds to a few minutes from each other, or over a more extended time period, wherein the pressurization of the load chamber 14 is performed at intervals of more than a few minutes to weekly or monthly intervals.

An example of a purely mechanical controller is shown for device 100 of FIG. 4, in which a push button 122 mounted to the compressed gas chamber 112 is used to activate a poppet valve 118 mounted through a wall 113 separating the compressed gas chamber 112 and the load chamber 114. The push button 122 may be used to move a piston 142 mounted on a bearing 140. The piston 142 operates the poppet valve 118. The poppet valve 118 includes a head 117 which, when pushed in the load chamber 114 allows the compressed gas to flow out of the compressed gas chamber 112 into the load chamber 114. The push button 122 may be spring biased so that a predetermined pressure exerted thereon is required to activate the poppet valve 118. The compressed gas chamber 112 may be refilled using a pressurized gas source through a gas inlet 22, for example provided with a one-way valve allowing to easily refill the compressed gas chamber 112. Any other suitable valve and actuator may also be used in alternative embodiments of the invention.

The load chambers 14 and 114 contain the powder 15 to be dispersed.

Figure 2:
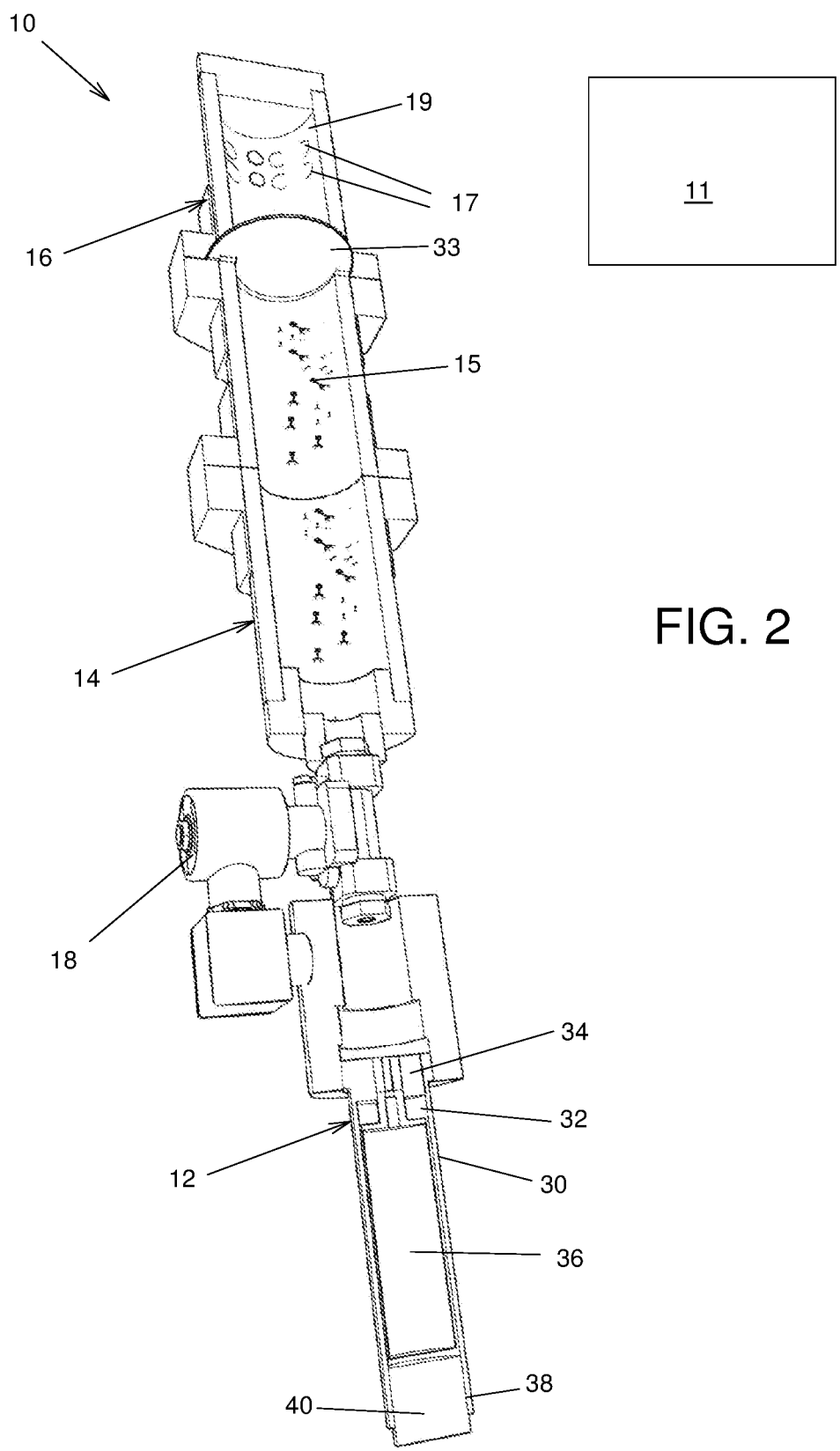
FIG. 2, in a longitudinal cross-sectional view with parts removed, illustrates the device of FIG. 1.
Figure 3:
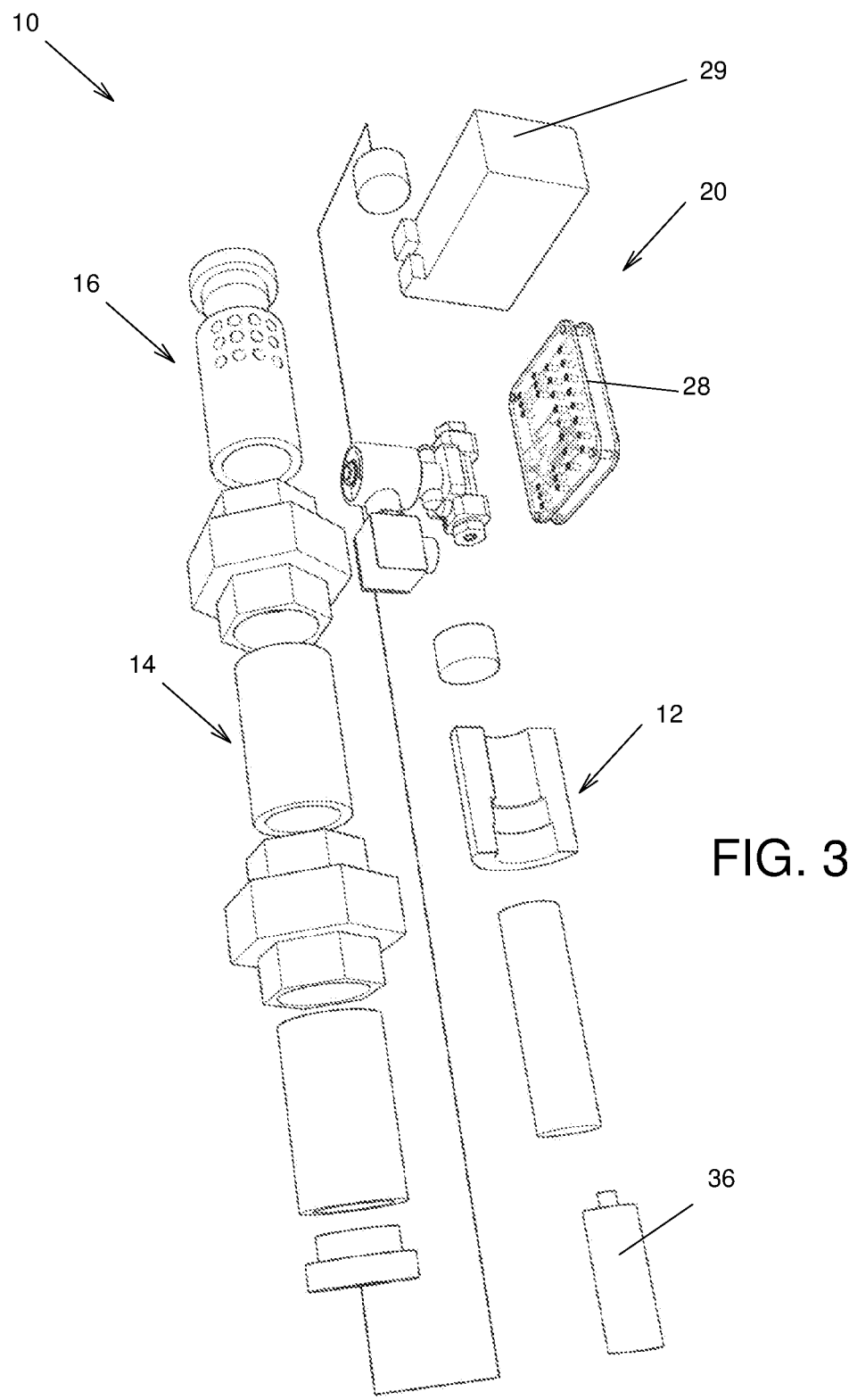
FIG. 3, in an exploded view, illustrates the device of FIGS. 1 and 2.
Figure 4:
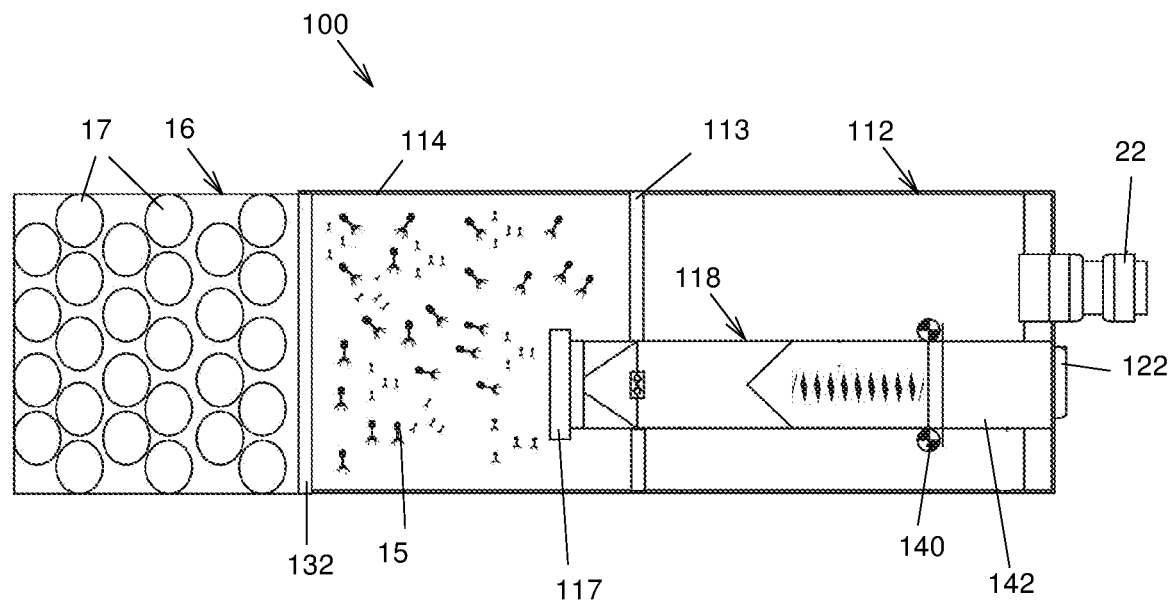
FIG. 4, in a schematic view, illustrates a device for dispersing a powder containing bacteriophages in accordance with an alternative embodiment of the present invention.

Reference will be made below to the load chamber 14 for simplicity, but the load chamber 114 operates similarly to the load chamber 14. These powders 15 could be provided directly into a load chamber 14 strong enough to withstand the relatively large pressures required for dispersion of the powder 15. In such cases, a diaphragm 33 or 132, seen in FIGS. 2 and 4 respectively, may extend between the powder 15 and the dispersion head 16, but in some embodiments, the diaphragm 33 or 132 is omitted. When present, the diaphragm 33 or 132 is made of material that is strong enough to confine the powder 15 in the load chamber 14 before the valve 18 is moved to the open configuration, but weak enough to be damaged or destroyed when the relatively large gas pressure of the compressed gas present in the pressurized gas source 12 is released in the load chamber 14. The diaphragm 33 or 132 may for example be made of relatively thin polymer or paper. In other examples, the diaphragm 33 or 132 is not destroyed in use and is a relatively sturdy mesh of a size small enough to prevent the powder from significantly exiting the load chamber 14 when the latter is not pressurized, but large enough to allow the powder to relatively easily be expelled from the load chamber 14 when the latter is pressurized.

In other embodiments, the diaphragm 132 is part of a capsule including the powder 15. Indeed, to facilitate handling of the fine particle loads, the powder 15 may come packaged in a capsule including an outer shell, made of a material similar to that from which the diaphragm 132 may be made, containing the powder 15. For example, the outer shell may be fragile enough to allow relatively easy penetration of the poppet valve head 117 thereinto when the valve is opened, which leads to sudden pressurization of the outer shell and release of the fine particles as the diaphragm 132 is damaged or destroyed.

The powder 15 may substantially entirely fill the load chamber 14, either relatively loosely or compressed. Alternatively, only a fraction of the load chamber 14 may be filled with the powder 15.

Returning to FIG. 2, the dispersion head 16 is for example of the type including a hollow internal chamber 19 from which a plurality of outlets 17, or nozzles, extend, leading to the atmosphere. The outlets 17 are dispersed on the outer surface of the dispersion head 16, for example in a substantially cylindrical or spherical configuration, among others. In some embodiments, the outlets 17 are dispersed around a segment of a cylindrical surface covering between about 60 and 180 degrees, so that the fine particles are projected generally upwardly when the surface of the dispersion head 16 opposed to the outlets 17 is facing the ground or a generally horizontal support surface. In other embodiments, the outlets 17 are configured to cause an omnilateral dispersion of the powder upon pressurization of the load chamber, for example by being dispersed along a cylindrical surface. In yet other embodiments, outlets are dispersed around a segment of a cylindrical surface covering between about 60 and about 180 degrees or between about 60 and 120 degrees, among others. Other outlet configurations are also within the scope of the appended claims. The internal chamber 19 is in fluid communication with the load chamber 14 (once the diaphragm 33 has burst, if needed for dispersion) so that when the latter is filled with compressed gas, the powder 15 are projected into the internal chamber and through the outlets 17.

In other embodiments, the load chamber 14 is filled with a liquid including bacteriophages, or with a liquid suspension of particles with bacteriophages adsorbed or dispersed in the particles and/or dispersed in the liquid. In some embodiments, the quantity of bacteriophages contained in each load of the load chamber 14 is sufficient to provide between about $10^4$ and $10^8$ PFU/m$^2$ on the surfaces to treat, but higher and lower quantities of bacteriophages are also within the scope of the invention.

Figure 5A:
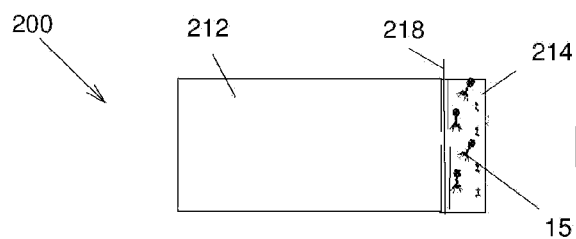
FIG. 5A, in a schematic view, illustrates a device for dispersing a powder containing bacteriophages in accordance with an other alternative embodiment of the present invention, the device being shown before activation.
Figure 5B:
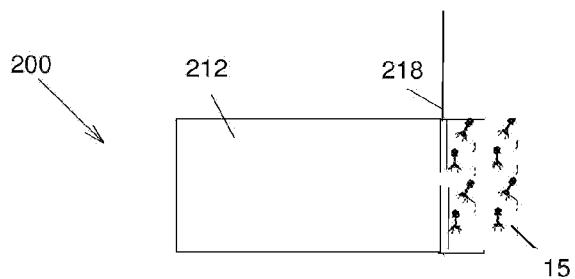
FIG. 5B, in a schematic view, illustrates the device of FIG. 5A after activation.

In yet other embodiments, a device similar to the devices 10 and 100 is single-use. In yet other embodiments, a device 200, seen in FIG. 5A, includes a load chamber 214 having at least part thereof that is too weak to withstand a high gas pressure separated from a compressed gas chamber 212 by a valve 218. The valve 218 may be a single use valve that allows the gas contained in the compressed gas chamber 212 to exit through the valve 218 when activated. This gas enters the load chamber 214 and damages, bursts, destroys or pulverizes at least part of the compressed gas chamber 212, which results in dispersion of the fine particles contained therein, as seen in FIG. 5B.

For example the valve 218 is simply a pin or other similar structure that obstructs an aperture extending between the load chamber 214 and compressed gas chamber 212 and which, when slid perpendicularly to the aperture, releases the gas. Other suitable valves 218 are usable.

Figure 6:
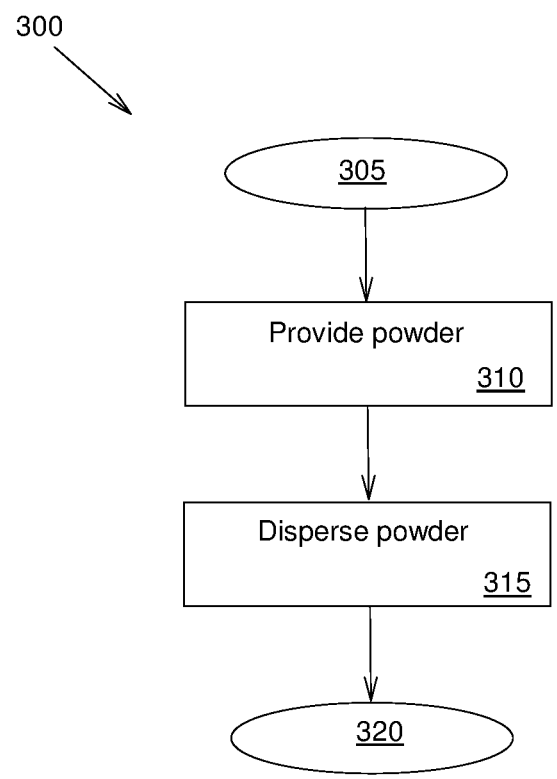
FIG. 6, in a flowchart, illustrates a method for using bacteriophages for at least partially disinfecting a surface exposed to air.

The above-described devices 10, 100 and 200, along with any alternative suitable devices, may be used to perform a method 300 using bacteriophages for at least partially disinfecting a surface exposed to air and illustrated in FIG. 6. The method starts at step 305. Then, at step 310, the method includes providing the powder 15, the powder 15 including bacteriophages. Subsequently, at step 315, the method includes dispersing the powder 15 in the air in proximity of the surface to apply at least part of the powder 15 on the surface. The powder is dispersed at a distance from the surface such that a significant portion of the powder will be able to reach the surface to disinfect. For example, the powder is dispersed adjacent the surface or up to many meters, 10 meters, or a few decameters away from the surface or even further away from the surface. The exact distance from the surface depends on the quantity of powder released, the release pattern and the speed at which the powder particles are released. The powder 15 is dispersed nonpyrogenically. In some embodiments, the powder is dispersed using a dry dispersion mechanism, that is in the absence of liquid, using only a gas. For example, the method 300 uses a sudden pressurization to a dispersion pressure larger than atmospheric pressure of a load chamber containing the powder 15 to expel the powder 15 from the chamber and form a cloud of powder suspended in the air, for example in the form of an aerosol.

Once in the air, part of the powder 15 may settle on the surface to treat. It should be noted that due to the small size of the particles, this surface may be at a relatively large distance from the powder release site, such as many meters or even more from the powder release site.

In some embodiments, the powder 15 may only include a small fraction of its mass in bacteriophages particles, for example between 1% and 50%, the remainder being in the form of auxiliary particles, and nevertheless remain effective. This is detailed in example 1.

Example 1

An SPK bacteriophage cocktail (active against *Staphylococcus aureus, Pseudomonas aeruginosa* and *Klebsiella pneumoniae* bacteria, $1.4 \times 10^9$ PFU/ml) was diluted 1/10 in Trehalose 0.5M and lyophilized using the following cycle and stored at 4° C.

| Temperature (° C.) | Rate (° C./min) | Time (h) | Comments |
|---|---|---|---|
| −40 | 0.67 | 1.3 | Put samples in |
| −40 | 0 | 3 | Vacuum on |
| 0 | 1 | 18 | |
| 25 | 0.07 | 6 | |
| 4 | 1 | Indef | Cap and Remove |

As a control of phage activity, 1 vial of lyophilized SPK cocktail (mean weight of 100 mg) was resuspended in 1 mL of sterile water and tittered SMQ-121 (SaX), ATCC15442 (PsA-159) and KP27 for *S. aureus, P. aeruginosa* and *K. pneumoniae* phages, respectively. The table below presents phage titer per mL and g of lyophilized phage powder.

| Bacteria | Titer (PFU/mL) | Titer (PFU/g) |
|---|---|---|
| *S. aureus* | 2.4E05 | 2.4E06 |
| *P. aeruginosa* | 2.3E06 | 2.3E07 |
| *K. pneumoniae* | 2.1E06 | 2.1E07 |
| Complete cocktail | 4.64E6 | 4.64E7 |

Lyophilized phage pellets were delicately broken with a sterile spatula and homogenized with high homogenizer to make a uniform fine powder, which had a final density of 0.33 g/cm$^3$.

Four additives (auxiliary particles) were used: Magnesium Sulfate (density 2.66 g/cm$^3$), Magnesium Carbonate (density 2.96 g/cm$^3$), Calcium Carbonate (density 2.71 g/cm$^3$) and TALC: (density 0.67 g/cm$^3$). Three dilutions of bacteriophages in additives were tested: 1:1, 1:10 and 1:100 of lyophilized phage powder in tested additives (w/w).

After mixing, activity testing was performed on 10 mg of lyophilized phage+additive mixture by pouring the powder on a layer of bacteria (1004 of bacterial culture at exponential phase in 2.5 mL of top agar). The bacteria used were SMQ-121 (SaX), ATCC15442 (PsA-159) and KP27 for *S. aureus, P. aeruginosa* and *K. pneumoniae* phages, respectively. Plates were incubated overnight at 37° C. before taking pictures with a gel doc system. In addition, negative controls of 10 mg of each additive and positive controls: of 10 mg of lyophilized SPK cocktail were used.

Figure 7A:
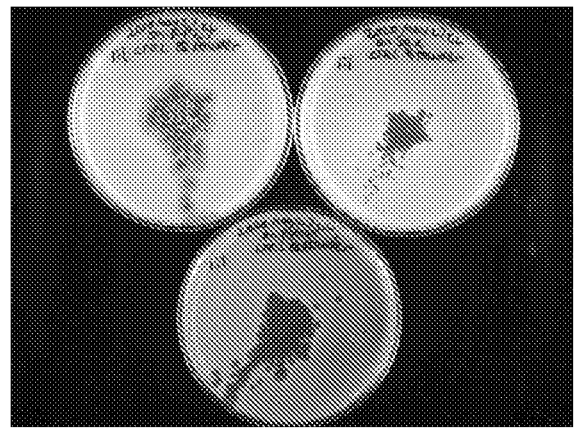
FIGS. 7A to 7D, in photographs of lysis patches on bacteria films, illustrate the results of phage activity tests on positive and negative controls in powder dilution tests.
Figure 7B:
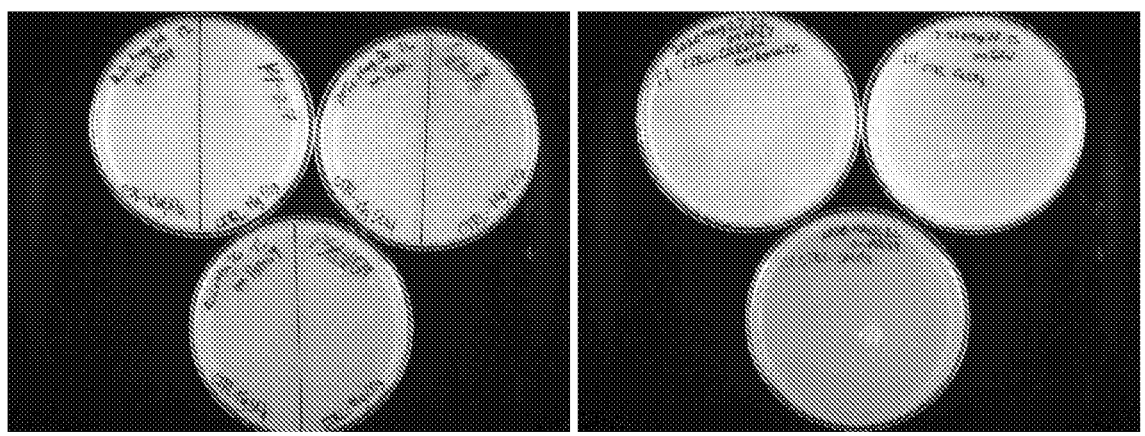
Figure 7C:
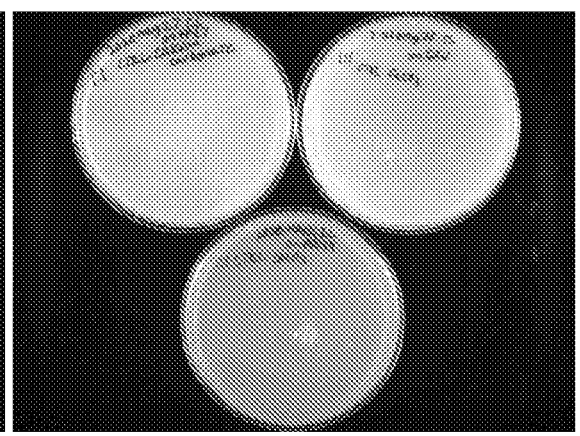
Figure 7D:
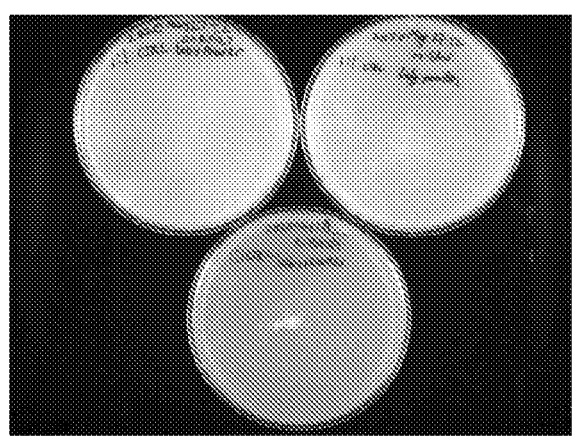
Figure 8A:
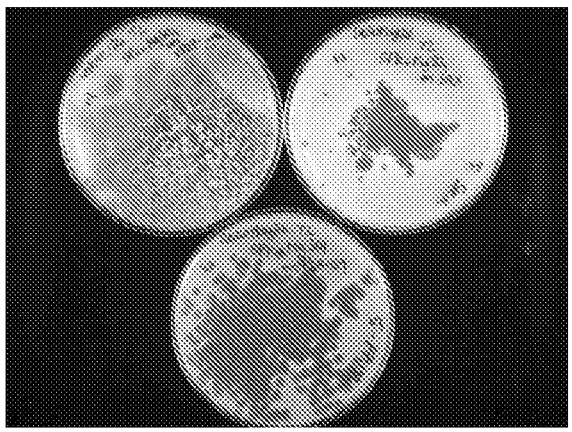
FIGS. 8A to 8D, in photographs of lysis patches of bacterial films, illustrate the results of phage activity tests on a dilution of a phage cocktail including 3 bacteriophages in 1:1 dilution in four different auxiliary powders.
Figure 8B:
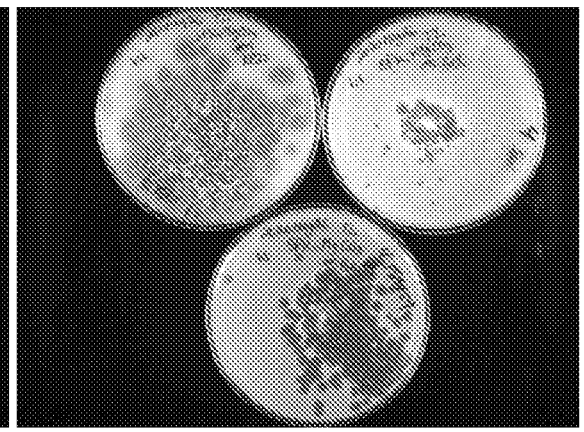
Figure 8C:
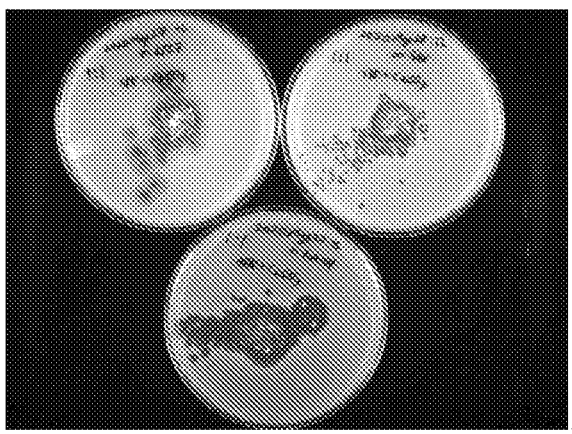
Figure 8D:
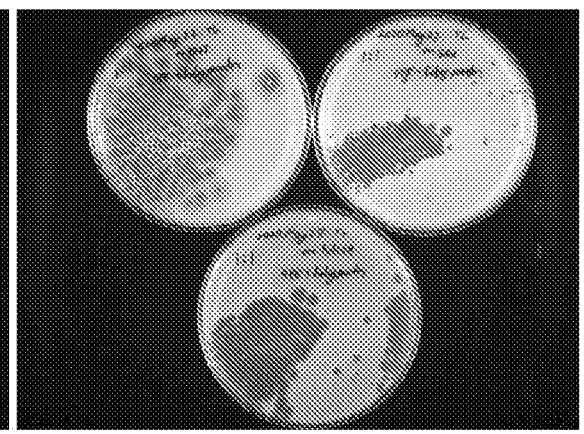
Figure 9A:
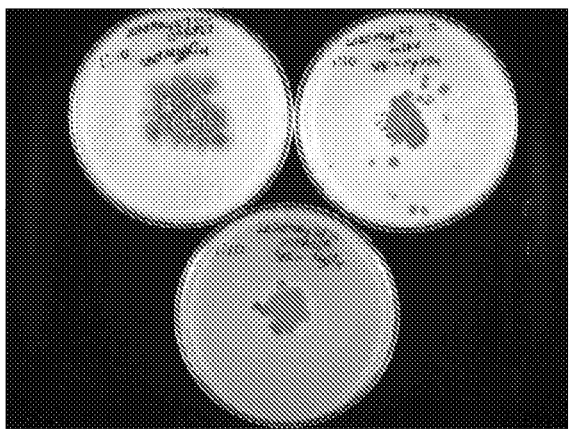
FIGS. 9A to 9D, in photographs of lysis patches of bacterial films, illustrate the results of phage activity tests on a dilution of a phage cocktail including 3 bacteriophages in 1:10 dilution in four different auxiliary powders.
Figure 9B:
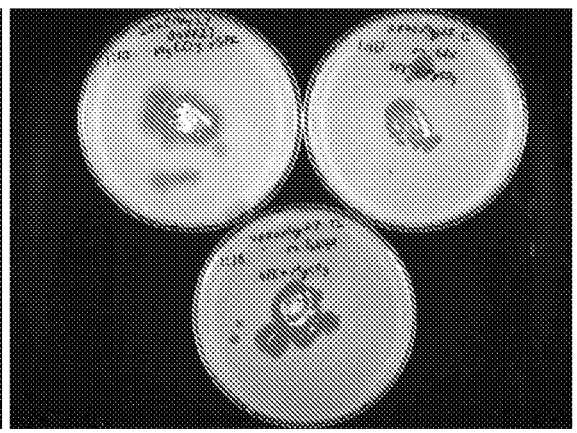
Figure 9C:
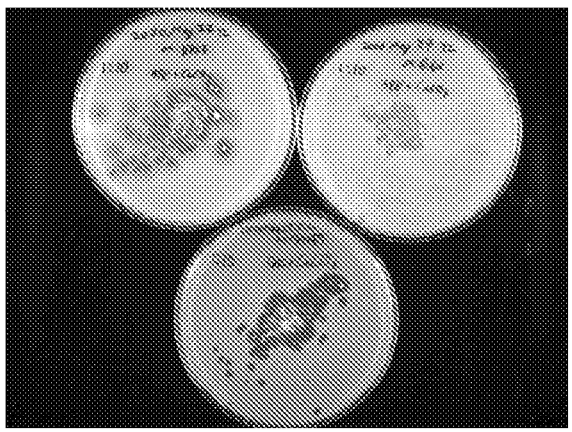
Figure 9D:
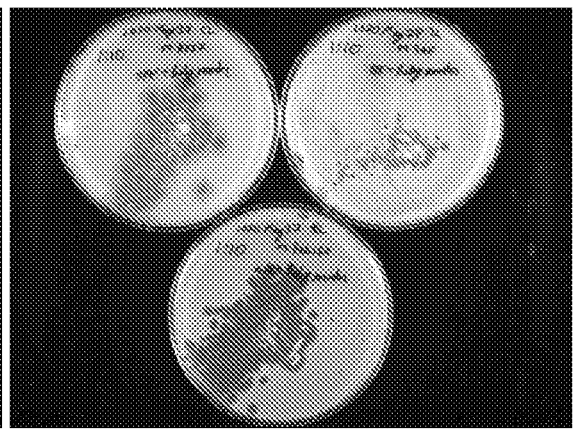
Figure 10A:
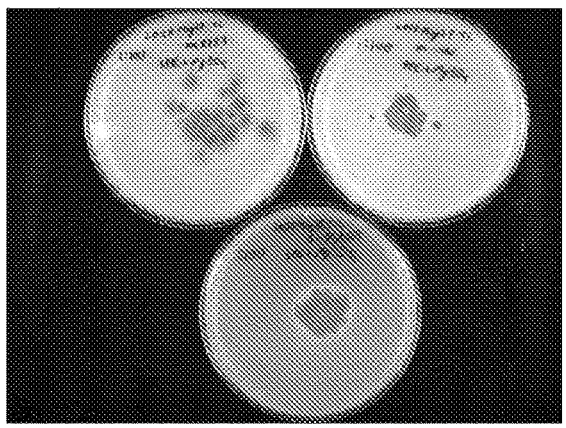
FIGS. 10A to 10D, in photographs of lysis patches of bacterial films, illustrate the results of phage activity tests on a dilution of a phage cocktail including 3 bacteriophages in 1:100 dilution in four different auxiliary powders.
Figure 10B:
Figure 10C:
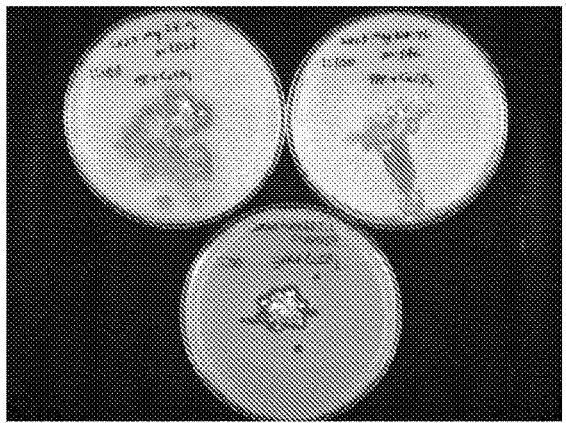
Figure 10D:
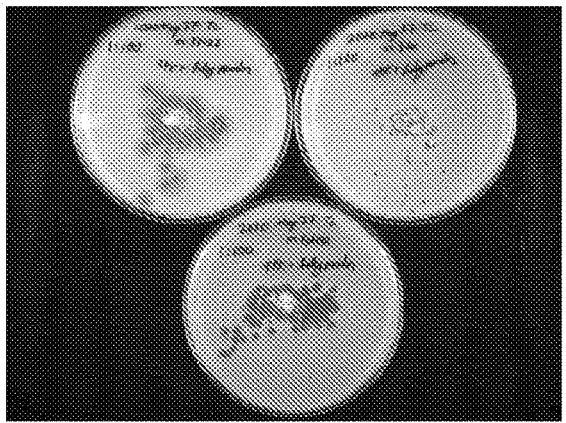

FIG. 7A to 7D represents the results of control experiments. Lysis is clearly visible on the positive control (FIG. 7A) and absent on the negative controls (FIGS. 7B to 7D). FIGS. 8A to 8D, 9A to 9D and 10A to 10D represent the results of phage activity in respectively 1:1, 1:10 and 1:100 dilution (w/w) of lyophylized phages in auxiliary powder (A: MgSO$_4$, B: MgCO$_3$, C: CaCO$_3$, D: talc). In all cases significant phage activity was detected. Lyophilized phages mixed with different additives were able to lyse bacterial lawns even at 1:100 ratio equivalent to 2.4E2, 2.3E3 and 2.1E3 pfu of *S. aureus, P. aeruginosa* and *K. pneumoniae* phages (each image includes one plate for each bacteria). Tested additives do not have any effect on phage activity but help spreading lyophilized phage powder more efficiently on the bacterial lawn.

Although the present invention has been described hereinabove by way of exemplary embodiments thereof, it will be readily appreciated that many modifications are possible in the exemplary embodiments without materially departing from the novel teachings and advantages of this invention. Accordingly, the scope of the claims should not be limited by the exemplary embodiments, but should be given the broadest interpretation consistent with the description as a whole. The present invention can thus be modified without departing from the spirit and nature of the subject invention as defined in the appended claims.

What is claimed is:

1. A method using bacteriophages for at least partially disinfecting a surface exposed to air, the method comprising:
   providing a powder, the powder including bacteriophages; and
   dispersing the powder in the air in proximity of the surface to apply at least part of the powder on the surface, wherein the powder is dispersed nonpyrogenically using a dry dispersion mechanism.

2. The method as defined in claim 1, wherein
   providing the powder includes providing the powder in a load chamber; and
   dispersing the powder includes pressurizing the load chamber to a dispersion pressure larger than atmospheric pressure to expel the powder out of the load chamber.

3. The method as defined in claim 2, wherein pressurizing the load chamber includes introducing a pressurized gas having a gas pressure larger than atmospheric pressure in the load chamber.

4. The method as defined in claim 3, wherein the load chamber is at least in part destroyed when the pressurized gas is introduced in the load chamber.

5. The method as defined in claim 2, wherein the powder is expelled out of the load chamber through at least one nozzle in fluid communication with the load chamber.

6. The method as defined in claim 2, wherein the load chamber is pressurized to between about 4 MPa and about 7 MPa.

7. The method as defined in claim 1, wherein the powder consists essentially of bacteriophages.

8. The method as defined in claim 7, wherein the bacteriophages are in the form of lyophilized bacteriophage particles.

9. The method as defined in claim 8, wherein at least 95 percent of the lyophilized bacteriophage particles in particle number has less than about 180 µm in size.

10. The method as defined in claim 9, wherein at least 95 percent of the lyophilized bacteriophage particles in number have more than about 10 µm in size.

11. The method as defined in claim 8, wherein at least 95 percent in mass of the lyophilized bacteriophage particles has less than about 180 µm in size.

12. The method as defined in claim 11, wherein at least 95 percent of the lyophilized bacteriophage particles in mass has more than about 10 µm in size.

13. The method as defined in claim 8, wherein at least 95 percent of the lyophilized bacteriophage particles in particle number has less than about 45 μm in size.

14. The method as defined in claim 8, wherein at least 95 percent in mass of the lyophilized bacteriophage particles has less than about 45 μm in size.

15. The method as defined in claim 1, wherein the powder further includes auxiliary particles.

16. The method as defined in claim 15, wherein the powder includes lyophilized bacteriophage particles dispersed in the auxiliary particles.

17. The method as defined in claim 16, wherein, the lyophilized bacteriophage particles make up from about 1 percent to about 50 percent in mass of the powder.

18. The method as defined in claim 15, wherein the auxiliary particles are selected from the group consisting of inorganic salt particles, hydrophobic polymer particles, silica particles, polyvinylpyrrolidone particles, cellulose ethers particles, polyethylene glycol particles, polyvinyl alcohol particles, poloxamers particles, $MgSO_4$ particles, $MgCO_3$ particles, $CaCO_3$ particles and talc particles, ionic surfactant particles, non-ionic surfactant particles, magnesium aluminometasilicate particles, cyclodextrins particles, magnesium stearate particles, starch particles, bactericide particles, detergents particles, antibiotics particles, nanoparticles, metallic powders particles, Ag particles, Cu particles, AgCu alloys particles, bimetallic nanoparticles, $FeO_4$ particles, $FeO_3$ particles, FeO particles superparamagnetic particles, and combinations thereof.

19. The method as defined in claim 15, wherein at least part of the bacteriophages are immobilized on the auxiliary particles.

20. The method as defined in claim 1, wherein dispersing the powder includes aerosolizing the powder.

21. The method as defined in claim 1, wherein the surface include one of a room surface inside a room, a vehicle surface inside a vehicle, an exposed wound surface, a conduit surface inside a conduit, an outdoors surface in the environment or combinations thereof.

22. The method as defined in claim 1, further comprising lysing bacteria present on the surface with the bacteriophages.

* * * * *